United States Patent
Zhang et al.

(10) Patent No.: US 12,188,009 B2
(45) Date of Patent: Jan. 7, 2025

(54) SIMPLIFIED METHOD FOR SIZE-PURIFICATION OF SMALL OLIGONUCLEOTIDES VIA GEL ELECTROPHORESIS

(71) Applicant: University of Cincinnati, Cincinnati, OH (US)

(72) Inventors: Xiang Zhang, Cincinnati, OH (US); Shuk-Mei Ho, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 263 days.

(21) Appl. No.: 16/469,242

(22) PCT Filed: Dec. 15, 2017

(86) PCT No.: PCT/US2017/066683
§ 371 (c)(1),
(2) Date: Jun. 13, 2019

(87) PCT Pub. No.: WO2018/112349
PCT Pub. Date: Jun. 21, 2018

(65) Prior Publication Data
US 2019/0352633 A1    Nov. 21, 2019

Related U.S. Application Data

(60) Provisional application No. 62/434,531, filed on Dec. 15, 2016.

(51) Int. Cl.
C12N 15/10    (2006.01)
C12N 15/11    (2006.01)
C40B 40/06    (2006.01)

(52) U.S. Cl.
CPC .......... *C12N 15/101* (2013.01); *C12N 15/111* (2013.01); *C40B 40/06* (2013.01); *C12N 2330/31* (2013.01)

(58) Field of Classification Search
CPC ............................ C12N 15/101; C12N 15/111; C12N 2330/31; C12N 15/10; C40B 40/06
See application file for complete search history.

(56) References Cited

U.S. PATENT DOCUMENTS

2010/0272803 A1* 10/2010 Mistry ................. C12N 5/0605
424/484
2010/0279305 A1   11/2010 Kuersten
2015/0051116 A1   2/2015 Kim

FOREIGN PATENT DOCUMENTS

WO    2016115001 A2    7/2016

OTHER PUBLICATIONS

Quail (BMC genomics (2014) vol. 15:110pp. 1-12).*
Lu (Methods (2007) vol. 43, pp. 110-117).*
Lee (Nature Communications ((2014) vol. 5: 3367, pp. 1-7).*
Locati ( Nucleic Acid Research (2015) vol. 43, e89, pp. 1-10).*
Mueller (RNA Integrity Number (RIN)-standardization of RNA quality control (2016).*
Havecker (Tamas Dalmay (ed.), MicroRNAs in Development: Methods and Protocols, Methods in Molecular Biology, vol. 732, DOI 10.1007/978-1-61779-083-6_5, © Springer Science+Business Media, LLC 2011).*
Zook (Plos One (2012) vol. 7, e41356, pp. 1-10).*
Vansant (DOI: 10.1200/jco.2013.31.15_suppl.11108 Journal of Clinical Oncology 31, No. 15_suppl (May 20, 2013) 11108-11108).*
Langevin (Oncotarget, 2017, vol. 8, (No. 47), pp. 82459-82474).*
Head (BioTechniques 56:61-77 (Feb. 2014) doi 10.2144/000114133).*
NEXTflex (TM) Small RNA Sequencing Kit v2; Nov. 1, 2014; Retrieved from the internet: http://www.biooscientific.com/portals/0/manuals/ngs/5132-03-NEXTflex-Small-RNA-Seq-Kit-v2.pdf.*
M.A. Quail et al, SASI-Seq: sample assurance Spike-Ins, and highly differentiating 384 barcoding for Illumina sequencing; BMC Genomics, Biomed Central, vol. 15, No. 1, Feb. 7, 2014; pp. 1-12.
S. Chaudhary et al, Small RNA Extraction Using Fractionation Approach and Library Preparation for NGS Platform; Journal of Advanced Research in Biotechnology; Apr. 12, 2016; pp. 1-5.
CAT Anonymous: Invitrogen by Life Technologies; 1 Kb Plus DNA Ladder; Jul. 17, 2013, pp. 1-2, Retrieved from the Internet: https://tools.thermofisher.com/content/sfs/manuals/1Kb_Plus_DNA_ladder_man.pdf.
T. Fiskaa et al, Distinct Small RNA signatures in Extracellular Vesicles Derived from Breast Cancer Cell Lines; PloS One: Aug. 31, 2016, vol. 11, No. 8, pp. 1-18.
M. Abbasian et al, Easy Method for Production of a Home-Made DNA Ladder in Every Laboratory; Advanced Biomedical Research, Mar. 25, 2015, vol. 4, No. 70, pp. 1-5.
Supplemental EP Search Report for corresponding EP Application No. 17 88 1276 mailed Jun. 23, 2020.
Communication pursuant to Article 94(3) EPC pertaining to corresponding European Patent Application No. 17881276.4 dated Jan. 17, 2022.

* cited by examiner

*Primary Examiner* — Steven Pohnert
(74) *Attorney, Agent, or Firm* — Dinsmore & Shohl LLP (57) ABSTRACT

Methods for simplified, rapid gel electrophoresis size-purification and downstream sequencing of an Oligo Library, for example an miRNA Library, based on co-purifying a DNA ladder molecular weight standard customized to co-migrate with Library to provide highly salient bands on the gel at the upper and lower ends of the Library size range, permitting precise cutting and avoiding the negative effects of gel distortion, variation of DNA migration rate in different lanes, and the difficulty of matching sample to ladder across a large distance. The methods may be applied to increase yield and purity in an Oligo Library of low-quality or low input Oligo, and in particular in small RNA samples.

11 Claims, 9 Drawing Sheets

Specification includes a Sequence Listing.

SIMPLIFIED METHOD FOR SIZE-PURIFICATION OF SMALL OLIGONUCLEOTIDES VIA GEL ELECTROPHORESIS

PRIORITY CLAIM

This application claims priority to U.S. Provisional Application No. 62/434,531, filed on 15 Dec. 2016, the entire disclosure of which is incorporated herein.

SEQUENCE LISTING

Applicant incorporates by reference a CRF sequence listing having file name 10738740_Seq_ST25.txt (1.95 KB), created Jul. 15, 2021.

TECHNICAL FIELD

The subject matter of the invention relates to novel molecular weight markers for gel electrophoresis and improved/simplified methods employing them in size purification of an oligonucleotide library for new generation sequencing.

BACKGROUND

Micro RNAs (miRNA) are short RNA oligonuceotides (Oligos) that regulate protein expression in cells by degrading or sequestering transcripts or by inhibiting translation. In next-generation miRNA sequencing (miRNA-seq), the entire population of miRNAs present in a biological sample is determined in parallel and can be used to examine tissue-specific expression patterns and associations with disease or to discover new isoforms of miRNA.

The likelihood that miRNA disregulation plays a role in cancer and other disease gives miRNA-seq the potential to become an important tool in diagnostics and prognostics, if costs can be brought down. Currently available miRNA-seq kits suffer from the disadvantage that they require high-quality samples at high concentrations, while extracting RNA from formalin-fixed paraffin-embedded (FFPE) and laser capture microdissection (LCM) samples or other bodily fluids often gives fragmented RNA with low yield.

Figure 1:
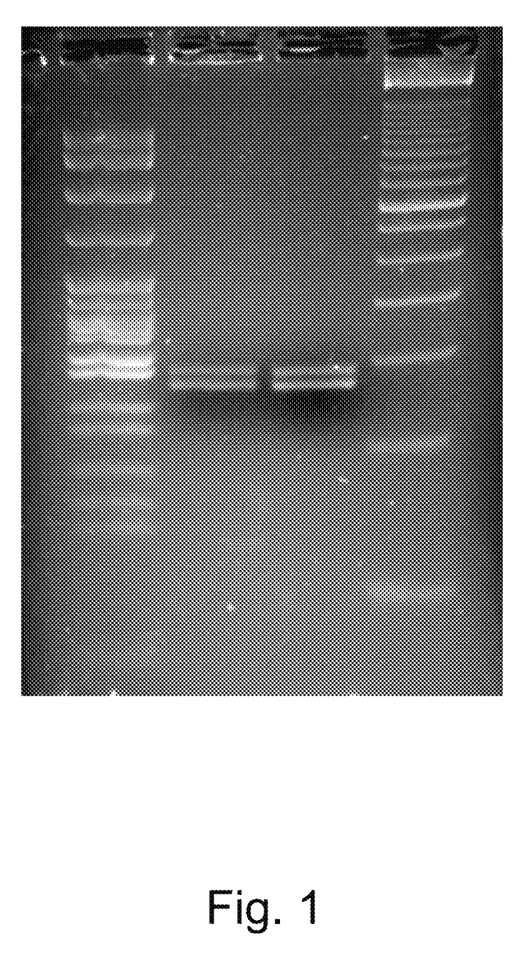
FIG. 1. PRIOR ART Image of gel demonstrating DNA migration retardation due to variation of salt concentration, specifically that the 147 bp fragment in lane 1 moves faster than the 146 bp DNA in lanes 2 and 3.
Figure 2:
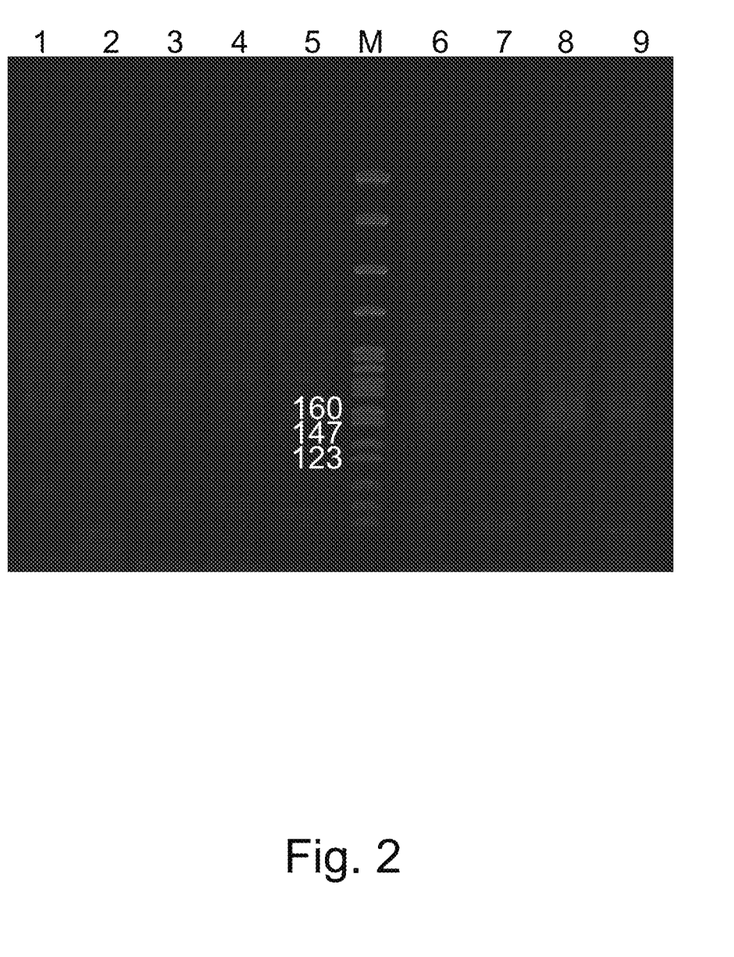
FIG. 2. PRIOR ART Image of gel showing that the DNA ladder (lane M) in commercially available kits cannot precisely indicate miRNA library position (135-146 bp) in gel, especially in those lanes farthest from the ladder (lanes 1 and 9).

While miRNA is stable, disadvantages of current protocols hinder the application of miRNA-seq to those samples. For example, PAGE gel library size selection is negatively affected by gel distortion. DNA migration retardation (FIG. 1), inaccurate long range size positioning (FIG. 2) and low library recovery yield. A non-size-specific ladder cannot precisely indicate the position in gel. Wider gel cut leads to decreased percentage of aligned reads. Variation of library size selection among samples may cause false positive results. Finally, low concentration of input RNA generates a low library concentration, which makes pooling of post-gel-purified library for sequencing more challenging.

Clearly, more precise methods for gel electrophoresis-based purification of small RNA libraries, and increased yield from low quality and low input samples sufficient for sequencing remain a need in the art.

SUMMARY

Accordingly, the present invention provides a novel and simplified approach for purifying and sequencing small RNA, for example, miRNA, from a library or sample using gel electrophoresis, and a unique DNA ladder molecular weight/size standard to generate aligned reads that are suitable for even low-quality and low-input RNA samples.

One embodiment is directed to a method for gel electrophoresis size-purification of a library of oligonucleotides (Oligos) comprising a size range of Oligos. Methods comprise co-purifying the Oligo library with an Oligo ladder molecular weight marker in a gel via electrophoresis, wherein the Oligo ladder marker is designed/selected to correspond in size to the size range of the Oligo library (or to a target subset of the library) and comprises molecules having nucleotide sequences that do not interfere with sequencing of the purified Oligo library. The methods are particularly suited to purifying a library of RNA Oligos, such as small RNA, microRNA (miRNA), and piwi-interacting RNA (piRNA).

Another embodiment is directed to a DNA ladder molecular marker suitable for gel electrophoretic methods of the invention, such as for co-purifying with a library of Oligos having a size range between X and Y base pairs. The DNA ladder molecular marker is selected/designed to form detectable bands on the gel corresponding to X bp and Y bp in order to visualize the precise location of the target library, located between X and Y, inclusive. The DNA ladder molecular marker consists of component DNA molecules having sequences that do not interfere with PCR sequencing of the target library of Oligos.

Another embodiment is directed to methods for gel electrophoresis size-purification of a small RNA library, said library comprising a size range of small RNA, the method comprising: providing a DNA ladder marker that corresponds to the size range of the small RNA library and consisting of DNA molecules having sequences that do not correspond to sequences of the small RNA library; mixing an amount of the DNA ladder with each sample of the small RNA library to be applied to a lane of the gel to yield at least one pooled sample; applying one pooled sample to each lane of the gel; and applying a current to the gel.

Another embodiment is directed to a method of sequencing a target library of small RNA such as miRNA comprising preparation of the library for sequencing according to the method of embodiments of the invention, further comprising cutting the gel between X and Y, inclusive, extracting nucleic acid from the cut gel and sequencing the extracted RNA. The DNA ladder is designed/selected so that it does not interfere with the sequencing of the small/miRNA.

Another embodiment provides an miRNA-seq kit for rapidly purifying and sequencing an miRNA library having a size range of miRNA between X bp and Y bp, the kit comprising a customized DNA ladder consisting of a molecular component that co-migrates with miRNA of size X bp, and a molecular component that co-migrates with miRNA of size Y bp in a gel during gel electrophoresis, said DNA molecular components comprising sequences of nucleotides that do not interfere with PCR sequencing of purified miRNA.

Embodiments of the inventive methods avoid the known negative effects of gel distortion, variation of DNA migration rate in different lanes, and the difficulty of matching sample to ladder across a large distance. Methods comprise co-purification of the ladder and small RNA which increases, e.g. miRNA library yield and enables the use of agarose gel electrophoresis in place of polyacrylamide gel, which simplifies the purification procedure even further.

These, as well as additional embodiments and aspect will be clarified and better understood by reference to the figures and detail description set forth below. Figures are provided to illustrate technical problems in the art as well as specific embodiments and aspects of the invention, and should not be construed as limiting the full scope of the claims appended hereto.

BRIEF DESCRIPTION OF THE FIGURES

FIGS. 3A-3C. Collectively demonstrate the ability to achieve a precise gel cut using an embodiment of the invention.

FIG. 5A-5C. A series of bar graphs demonstrating that miRNA-seq data from low quality and low input RNA exhibits good alignment result with good reproducibility when purified according to embodiments of the invention.

DETAILED DESCRIPTION

The present disclosure provides a novel and simplified approach to solve known deficiencies in the art of by gel electrophoretic techniques, and in particular as applied to purification and sequencing of small RNA libraries.

One embodiment provides methods for gel electrophoresis size-purification of a library of oligonucleotides (Oligos), said library comprising a size range of Oligos, the method comprising: co-purifying an Oligo ladder molecular weight marker with the Oligo library in a gel via electrophoresis, wherein the Oligo ladder marker corresponds to the size range of the Oligo library and comprises a nucleotide sequence that does not interfere with sequencing of the Oligo library. In accordance with specific aspects, the library of Oligos comprises a library of small RNA, wherein "small" RNA is customarily defined having less than 250 nucleotides. In other specific embodiments, the Oligo Library comprises microRNA Library, and in other specific embodiments the Oligo Library comprises piwi-interacting RNA (piRNA).

Figure 6:
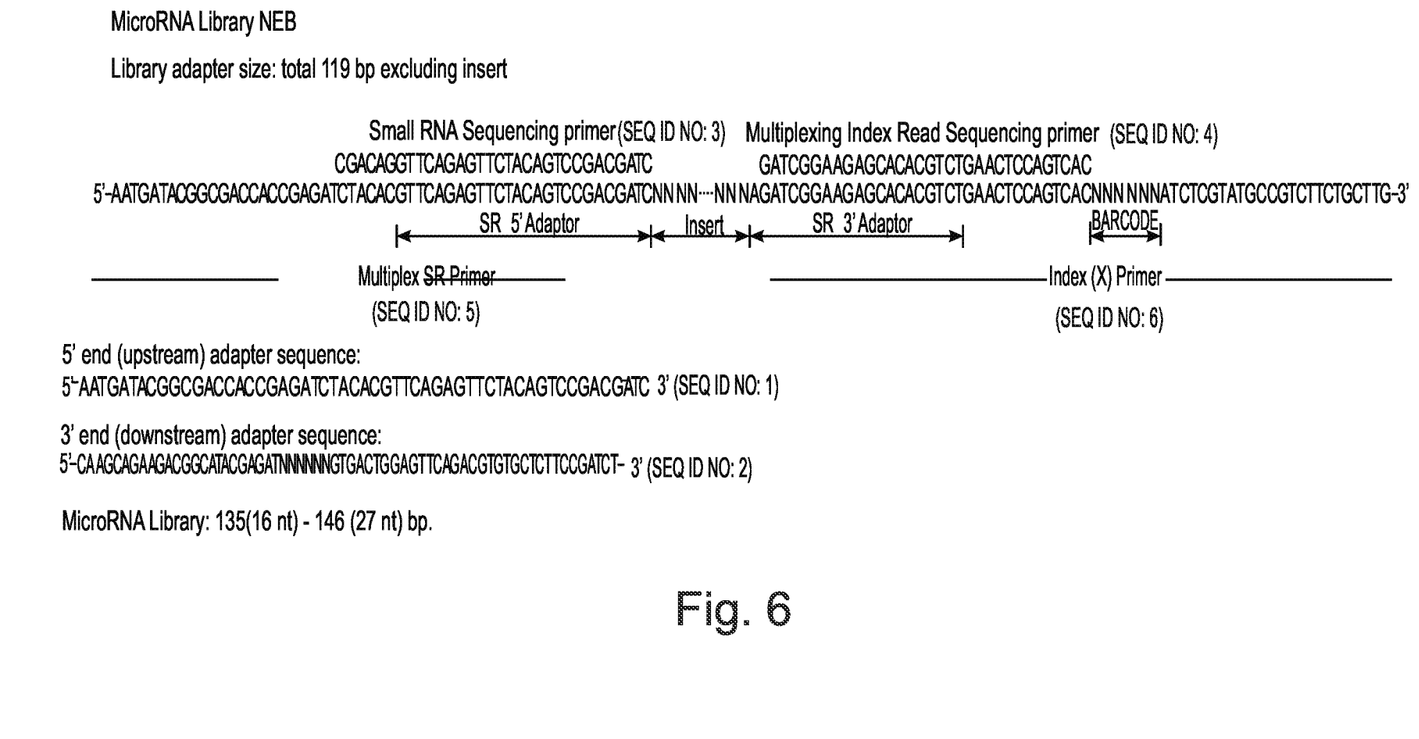
FIG. 6. Exemplary sequence adapter for miRNA Library, specifically the Illumina™ adapter for the NEB miRNA Library, showing the origin of the 119 base pair sequence.

MicroRNAs are single stranded RNAs consisting of about 16-27 nucleotides (nt). More precisely, the number of nucleotides in a human mature miRNA is a discrete random variable, which ranges from 16 to 27 with a mode and median of 22 (Zhide, F. et al. "The Sequence Structures of Human microRNA molecules and their implications" PLOS Jan. 18, 2013, the entire disclosure of which is incorporated herein by reference). When preparing a double-stranded miRNA library, however, sequencing adapters are added to both ends of miRNAs' double-strand cDNAs such that miRNA double-strand cDNAs+sequencing adapters on both ends of the cDNAs=the miRNA library. Suitable sequencing adapters are available from various manufactures (e.g. Illumina sequence adapters) and are designed for optimal use with the proprietor's sequencing technology. In specific examples set forth herein, a New England Biolabs NEBnext small RNA Library prep kit is utilized with Illumina brand sequence adaptors having a size of 119 bp (see FIG. 6). Thus, for very specific embodiments wherein size of the miRNA Library is set forth as from 135 to 146, this actually corresponds to miRNA having a size range of 16-27 (135=16+119; 146=27+119 bp). It is understood, however, that the size range of the Library may vary based on the selection of a specific sequence adapter and thus may be adjusted accordingly by the simple addition algorithm set forth above. Further, subsets of the size range are contemplated such that a target subset may include the full size 11 value range of 16-27, or any 2-member, 3-member, 4-member . . . up to 10 member subset. Similarly, piwi-interacting RNA is defined as non-coding RNA having between 26 and 31 nt length, and purification/sequencing according to embodiments of the invention comprises a similar adjustment of the size range to account for a specific sequence adapater. It is clear to a person of ordinary skill in the art that the simple adjustment may be made with any size range of RNA.

Thus, as is understood by a person of ordinary skill in the art, the prepared miRNA library (double-stranded DNA) and not the single stranded microRNA co-migrates with embodiments of the custom made DNA molecular standard.

"Corresponding to the size range," as used herein, means that the lighter component of the DNA ladder is selected to correspond in size, and therefore end migration position, of the lower end of the target Oligo Library size range, and the heavier component of the DNA ladder is selected to correspond in size, and therefore end migration position, of the upper end of the target library size range. Thus, if the Oligo library comprises target purification Oligos having a size range of from X to Y base pairs, then the Oligo ladder comprises, or in very specific embodiments, consists of molecules with X base pairs and molecules with Y base pairs.

Since the total RNA (sample input) contains different types of RNAs or degraded RNAs with different lengths, the prepared library is a mixture with different sizes that represents these RNAs. In order to effectively sequence the miRNA library, other sizes of library and other RNAs in the mixture need to be precisely removed (as provided by embodiments of the invention via co-migration of a custom made DNA standard) and the miRNA library needs to be efficiently recovered (as provided by embodiments of the invention via co-purification of the custom made DNA standard from the gel). The novel methods disclosed herein enable easier, simpler and more efficient miRNA-seq using degrade low input RNA samples much easier and more efficient.

In the state of the art of gel electrophoresis, a DNA ladder is used as a standard size marker to determine size-by-position of migrated miRNA library in the gel. However, the ladder is not usually designed/sized to exactly match a target miRNA library size range. Custom-sized DNA ladders for some purposes are known in the art, but the present investigators are unaware of DNA ladders designed specifically for co-migration with the target Library, and existing ladder migration is conducted in a lane distinct from the sample so as not to interfere with the purification and sequencing of the target.

One aspect of the inventive methods is selection or design of a custom Oligo ladder molecular weight marker. It is important for the ladder to be selected such that it does not interfere with downstream sequencing of the purified, extracted target Library. In some embodiments, the Oligo Ladder sequences are different than the target Oligo library sequences. According to specific embodiments, the Oligo ladder comprises or, in very specific embodiments, consists of two sizes of nucleic acid molecules selected to precisely define both the upper and lower ends of the size range of the target Oligo library when co-migrated in the gel. According to specific embodiments, the Oligo ladder marker comprises a DNA ladder. Embodiments of the invention provide that purposes of precisely locating cutting positions for purification of the target Oligo Library in the gel, resolution of the input Oligo Library is no longer important because cutting demarcation is located at the gel migration positions of the DNA ladder. Therefore the target library may be generated from low quality or a reduced amount of input nucleic acid, such as low quality or low input RNA. According to specific aspects, low quality is defined as Bioanalyzer RIN<7, and reduced amount is defined as <100 ng in 6 µl. "Does not interfere with downstream sequencing . . . " means that there is no sequence similarity between the DNA ladder marker and the adapter sequence utilized for the Library such that the custom DNA ladder marker cannot be sequenced on a platform without possessing the adapter sequence used for the Oligo Library. As a specific example, where the Oligo Library is an miRNA Library and the sequence adapter is the 119 base pair Illumina™ adapter set forth in FIG. 6 (5' end of miRNA cDNA insert: 5'—AATGATACGGCGAC-CACCGAGATCTACACGTTCAGAGTTCTA-CAGTCCGACG ATC-3' (SEQ ID NO: 1); 3' end of miRNA cDNA insert: 5'—CAAGCAGAAGACGGCAT-ACGAGATNNNNNNGTGACTGGAGTTCAGACGTGT GCTCTTCCGATCT-3' (SEQ ID NO: 2), the DNA ladder marker cannot be sequenced on the Illumina platform.

Embodiments of the invention provide novel, customized DNA ladder molecular markers, which are suitable for gel electrophoresis of small RNA, micro RNA, and piwi-interacting RNA, for example, and which are particularly suitable for miRNA-seq technology/processes. According to one embodiment, a DNA ladder is customized for gel-purification of a target small RNA Library having a size range between X and Y base pairs, and the DNA ladder molecular marker consists of DNA molecules of X base pairs in size, and DNA molecules of Y base pairs in size, wherein the DNA molecules have a nucleotide sequence that will not interfere with PCR sequencing of the small RNA Library. According to very specific embodiments, the Oligo Library is a microRNA library. X is 135 and Y is 146.

Embodiments of the invention overcome deficiencies related to use of the safer, higher-through-put agarose gels for size purification of small Oligo Libraries, and especially of low-quality or low-input Libraries, since concentration of agarose demanded by very small sized nucleic acid migration is typically so high that results are distorted. Polyacrylamide (PA) gels are therefore typically preferred for higher resolution needs; however the preparation time of the PA gel is greater, the gel typically must be run vertically, and library recovery from the gel with high yield is technically challenging and time-consuming.

As noted, in conventional library purification, the DNA ladder and PCR amplified library (including other sizes of nucleic acid) are loaded in different lanes in the gel. Gel distortion, salt and other impurities in the sample which affect DNA migration rate and the distance of the sample lane from the marker lane interfere with precise determination of the position of miRNA in the gel. Pooled, amplified PCR products are not used in gel electrophoresis. Different samples are loaded in different lanes for individual gel cutting. Variation in cutting results in sample-to-sample variation. Further, the currently available methods require high quality (Bioanalyzer RIN>7) and high input amounts of RNA (>/=100 ng in 6 µl).

Embodiments of the invention substantially eliminate the guesswork present in gel electrophoresis for miRNA library size selection. Novel customized DNA ladders may be provided that are mixed with the PCR sample for co-migration with the Library in the gel. For example, a novel DNA ladder comprising 135 bp molecules and 146 bp molecules suitable for use with the NEB small RNA library preparation kit have been developed based on the disclosed parameters such that the migrating ladder components do not interfere with downstream sequencing. According to specific embodiments, a novel DNA ladder is designed to exactly match a desired miRNA library size range.

Method embodiments provide precisely-guided positioning for purification/gel cutting. Migration of the ladder components result in detectable upper and lower bands framing the portion of the gel containing the migrated target Oligos between them. For example, a novel DNA ladder may be mixed with amplified miRNA library product (with other sizes of unwanted cDNA co-amplified) for precise gel cutting in the library size selection. The negative effects of gel distortion, variation of DNA migration rate in different lanes, and the effect of distance from sample to ladder are all eliminated.

One embodiment is directed to methods for gel electrophoresis size-purification of a small RNA library, the library comprising a size range, the method comprising: providing a DNA ladder marker comprising molecular components having a size that corresponds to the size range of the small RNA Library and having sequences that do not correspond to a sequence of the small RNA Library; mixing an amount of the DNA ladder with each sample of the small RNA Library to be applied to a lane of the gel to yield at least one pooled sample; applying the pooled sample to a lane of the gel; and applying a current to the gel. "Corresponds to the size range" means that if the Library comprises a target small RNA Library having a size range of from X base pairs to Y base pairs, then the DNA ladder comprises, or in specific embodiments consists of, DNA molecules of X base pairs and DNA molecules of Y base pairs in size. The molecular components of the DNA ladder co-migrate with corresponding-sized miRNA and form a band at X base pairs and a band at Y base pairs, with the small RNA Library migrating from X to Y, inclusive and being located within the band. According to very specific embodiments, the gel is agarose. According to specific embodiments, X is 135 and Y is 146. In some embodiments, the methods further comprise cutting the gel between X and Y, inclusive, and in some embodiments, further extracting purified target small RNA Library from the cut gel and sequencing the extracted Library.

Another embodiment is directed to kits for practicing method embodiments. According to one embodiment, an miRNA-seq kit is provided for rapidly purifying and sequencing an miRNA Library having a size range between X bp and Y bp, the kit comprising a customized DNA ladder consisting of a molecular component that co-migrates with X bp sized miRNA, and a molecular component that co-migrates with Y bp sized miRNA in a gel during gel electrophoresis, said molecular components comprising a sequence of nucleotides that does not interfere with PCR sequencing of purified miRNA Library. In some embodiments, the kit further comprises a gel or reagents for making a gel, and in more specific embodiments the gel comprises an agarose gel or reagents for making an agarose gel.

Embodiments disclosed herein provide a simplified gel purification process with reduced experimental time and increased library yield. Precise library positioning in the gel reduces sample to sample variation during gel cutting. Further, amplified library PCR products from different samples can be pooled (optionally with different indices from different samples) and size-selected in the same lane, which further reduces sample to sample or lane to lane variation during size selection.

Embodiments of the invention provide for reduced workload in Oligo library purification and quantification. Instead of running a library qPCR quantification assay for each sample, quantification of one pooled gel-purified library from multiple samples can be established. Based on initial sequence alignment results, the volume of each library PCR product can be adjusted in a new pre-gel purification pool. Using single qPCR quantification for gel-purified pooled library, the expected number of aligned reads form each sample can be generated.

Pooling amplified library considerably reduces required library concentration or PCR cycle numbers in individual sample and experimental hands-on time. Less PCR cycle numbers means reduced PCR bias and unwanted duplicate reads in sequencing, and therefore improved data quality.

The improved purification and sequencing methods disclosed herein are particularly useful when applied to low quality and low input source RNA, such as those from body fluid, exosome, clinical or animal FFBE tissue. Embodiments of the invention exhibit the ability to process very low quality of RNA and very low concentrations and total amounts of RNA. In specific embodiments the methods may be practiced from an initial RNA sample having low quality (defined herein as a bioanalyzer RIN score close to 1) and low-input (defined herein as concentrations less than 15 ng in 6 µl) RNA samples. Other small RNA such as piwi-interacting RNA can also be processed in the same way by adjusting design of the molecular marker ladder size to match piwi or other small RNA size.

Example

To illustrate embodiments of the invention, a novel DNA ladder matching a desired miRNA Library size range (according to one specific illustrative example, 135-146 base pairs for the New England Biologics (NEB) small RNA library preparation kit utilizing a 119 Illumina sequence adapter (see FIG. 6 and the workflow for preparation of the Library set forth in detail at www.neb.com/applications/library-preparation-for-next-generation-sequencing/illumina-library-preparation/rna-for-illumina as accessed on the filing date of this application) is generated that eliminates guesswork in gel electrophoresis for miRNA Library size selection/purification, without interfering in the downstream sequencing of the Library. The custom DNA ladder is designed to co-migrate with the miRNA Library, and to comprise DNA molecules that migrate to form precise bands in the gel at both ends of the miRNA Library size range. The custom DNA ladder is mixed with amplified miRNA library products to guide the precise gel cutting during library size selection. This procedure avoids the negative effect of gel distortion, variation of DNA migration rate in different lanes and the difficulty of matching sample to ladder across a large distance. Co-purification with the ladder increases miRNA Library yield and enables the use of agarose gel electrophoresis in place of polyacrylamide gel, which further simplifies the purification procedure. The precise Library size-positioning in the gel reduces sample-to-sample variation during gel cutting and pooling, and size selection in the same lane of amplified library PR products further reduces sample-to-sample lane-to-lane variation. Pooling also considerably lowers the required Library concentration or the number of PCR cycles needed in an individual sample (which minimizes PCR bias and unwanted duplicate reads in sequencing, thereby improving data quality). Overall sequencing cost is also lowered by the exclusion of DNA sequences of unwanted length (<135 base pairs or >146 base pairs).

Initial alignment results suggest that the volume of each Library PCR can be adjusted in a pre-gel purification pool, thus avoiding the need for individual gel purification and a qPCR quantification assay on each sample. Instead, a single PCR quantification step for the gel-purified pooled Library generates the expected number of aligned reads from each sample. This considerably reduces both the required Library concentration in each sample and the hands-on time to conduct the experiment.

Figure 3A:
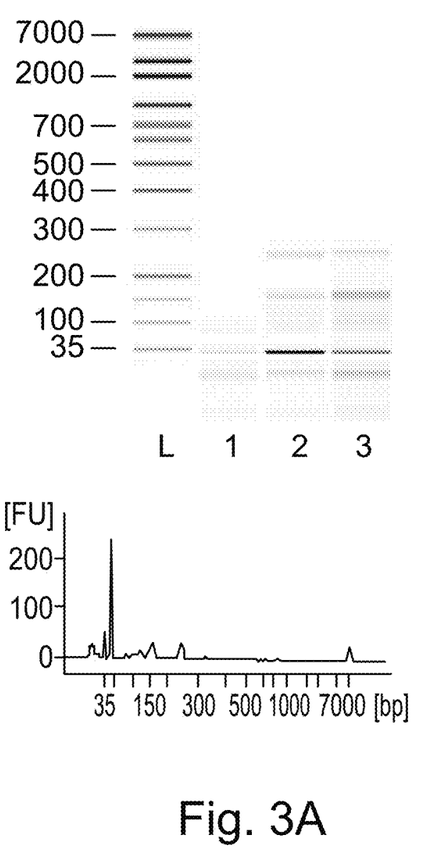
FIG. 3A) A gel image and bioanalyzer QC trace/readout of a pre-purified library PCR pool having a wide range of non-miRNA in the library (<135 bp and >146 bp)
Figure 3B:
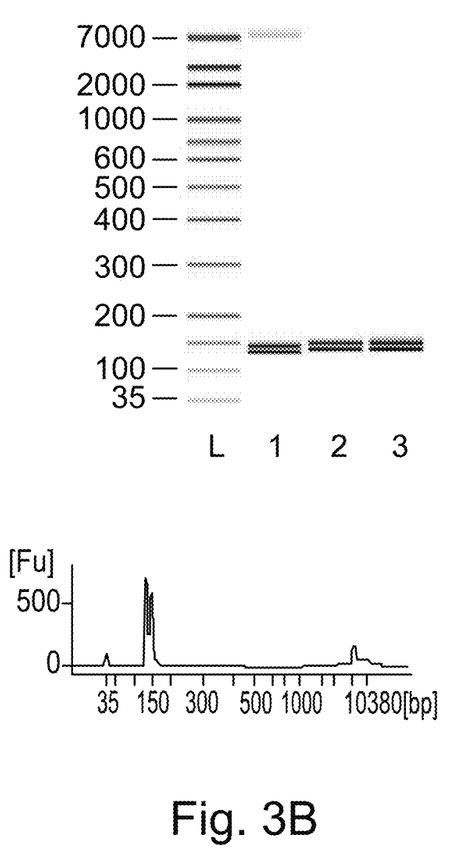
FIG. 3B) A gel image and bioanalyzer QC trace/readout after agarose gel excision and purification of a mixture of a size-specific DNA ladder and the library PCR pool to achieve a precise gel cut of miRNA libraries (135-146 bp)
Figure 4:
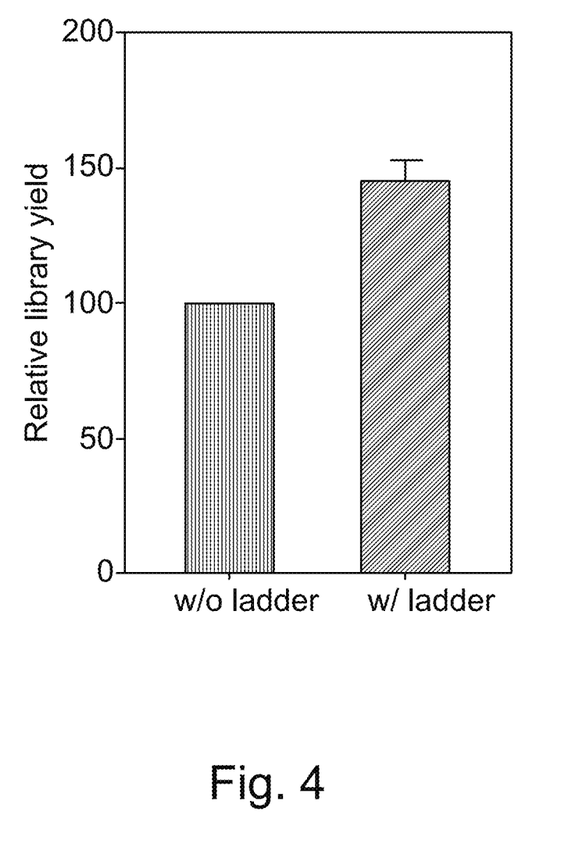
FIG. 4. Bar graph showing an increase in relative percent yields when electrophoretic purification is performed with versus without a custom in-sample ladder according to a specific embodiment. The graph demonstrates that the ladder with a sequence selected to be different than the target library acts merely as a DNA carrier during gel purification without affecting downstream sequencing.

Co-purification of the ladder with the Library not only increased library yield as shown in FIG. 4, but permits purification of a low-resolution library, as can be seen in FIG. 3B. In addition, Library PCT from different samples may be pooled and size-selected in the same lane in a gel, which eliminates sample-to-sample variation.

Based on the initial alignment result, the volume of each library PCR can be adjusted in a new pre-gel-purification pool. Without individual gel purification and qPCR quantification, the expected number of aligned reads from each sample can be generated. This considerably reduces required library concentration in each sample and labor/handling time. Further, the resulting sequencing data is of higher quality. Sequencing nucleic acid of unwanted length (e.g. <135 bp or >145 bp in the specific example) is significantly reduced.

Figure 3C:
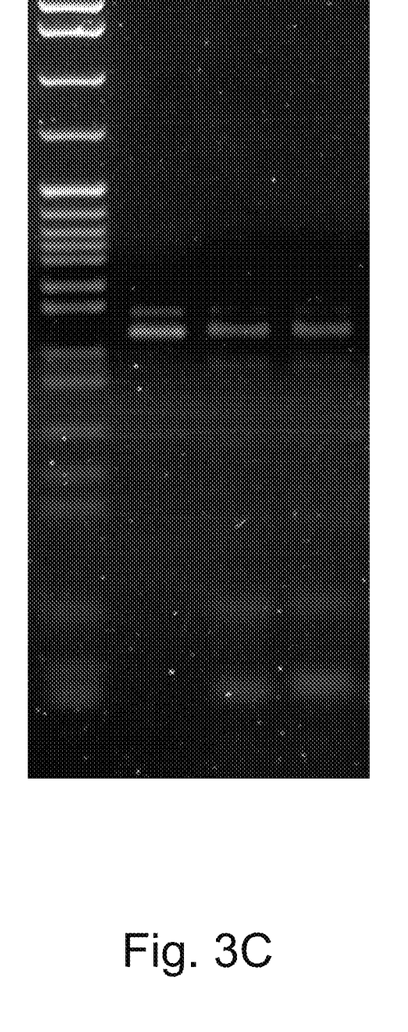
FIG. 3C) image of the pre-purified library PCR pool and custom-made ladder mixture in agarose gel after electrophoresis.

With reference to FIGS. 3A-3C; FIG. 3A shows results of a gel run without the custom made ladder present in the sample, and illustrates the difficulty/inability to get a precise alignment/cut, resulting in inclusion of many non-target Oligos in the Library PCR. FIG. 3B sets forth the results of co-purification of a custom-made DNA ladder (for an miRNA Library made with an Illumina 119 bp sequence adapter, specifically exemplified by 135 and 146 bp) with samples of the miRNA Library, providing highly salient upper and lower bands encompassing the area of the gel comprising the target miRNA Library after co-migration. The custom DNA ladder is mixed with the almost invisible pre-purified Library PCR pool as an in-lane marker for precise gel cutting of a 135-146 bp size range, the same size range of the target miRNA Library. Further, because precision of the cut is so high despite the poor resolution of the target Library on the gel, agarose may be utilized. The ability to use agarose gel instead of other longer-setting, vertically run gels, such as polyacrylamide/PAGE gel also simplifies the Library purification. Ordinarily agarose is not a first-choice for very small oligo gel size purification due to the high concentration of agarose required and poor resolution.

Figure 5A:
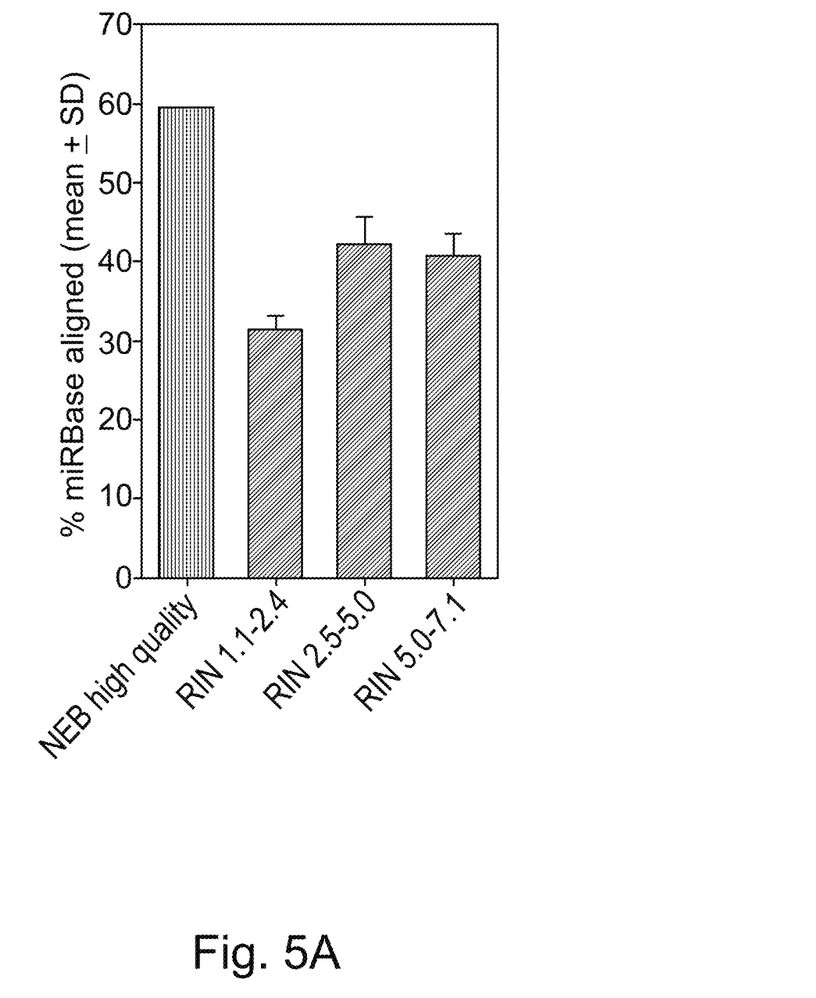
FIG. 5A) a bar graph of miRNA alignment % as a function of RNA integrity number (RIN)
Figure 5B:
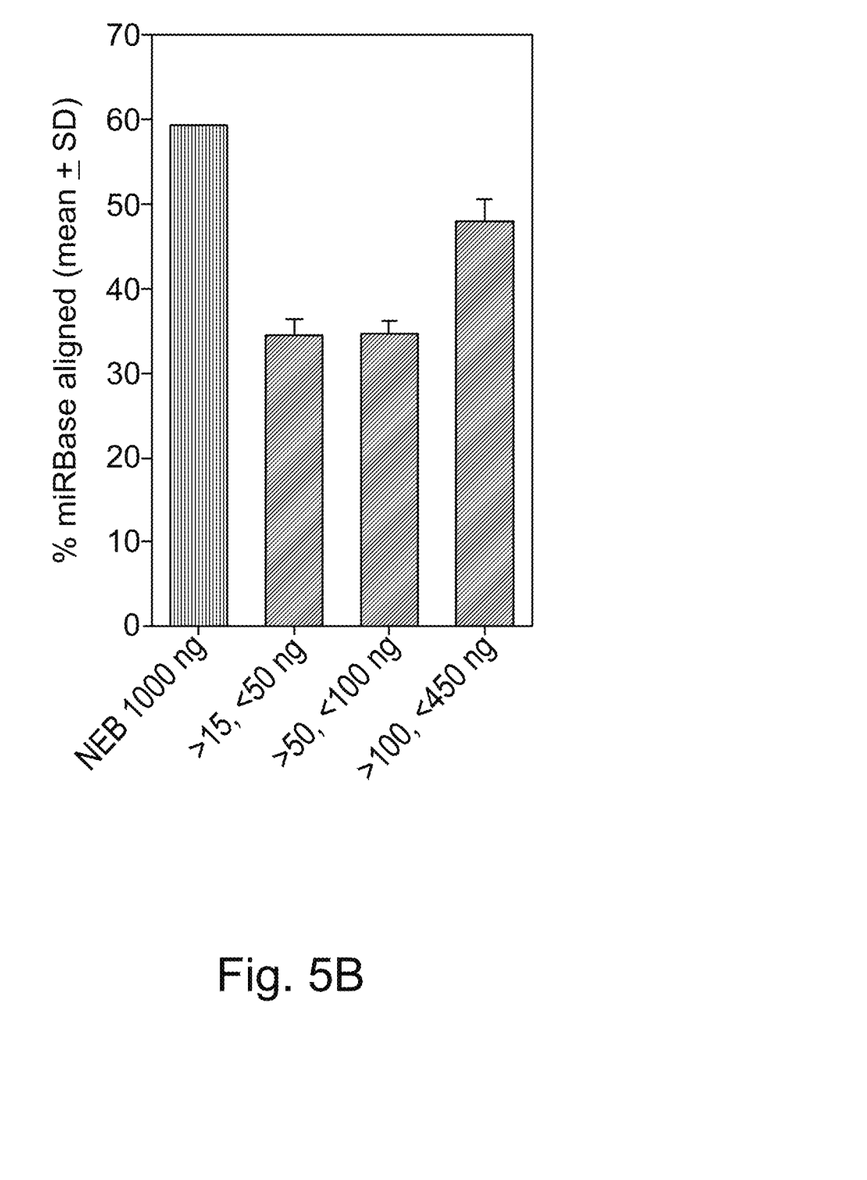
FIG. 5B) a bar graph of miRNA alignment % as a function of input amount.
Figure 5C:
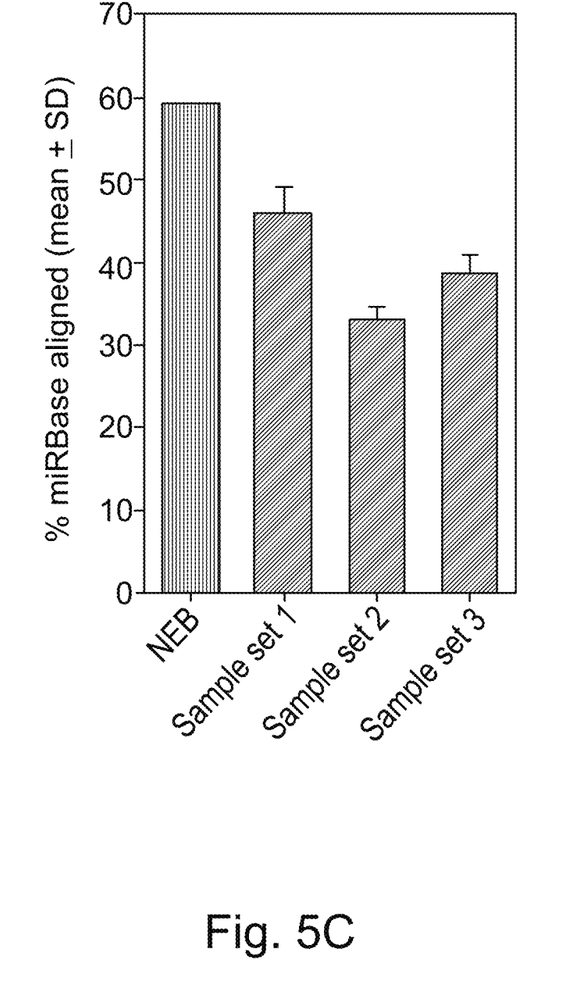
FIG. 5C) a bar graph of miRNA alignment % as a function of sample.

FIG. 4 shows that co-purification of the in-sample ladder improves Library recovery from gel. The custom DNA ladder with an unrelated sequence acts as a DNA carrier during gel purification without affecting downstream sequencing. FIGS. 5A-C sets forth the result of runs on varying amounts and quality miRNA Library and shows that miRNA-seq data from low quality and low input RNA Library samples exhibits good alignment results and excellent yield with good reproducibility.

The invention claimed is:

1. A method for identification of a microRNA library, said microRNA library comprising microRNA of a size range of 16 nucleotides (nt) in length to 27 nucleotides in length, the method comprising:
   a) adding a 3' adaptor to microRNA of an RNA sample;
   b) adding a 5' adaptor to microRNA of the RNA sample;
   c) generating a cDNA thereof and amplifying the cDNA by polymerase chain reaction (PCR);
   d) mixing a DNA ladder with pooled cDNA from c), wherein the DNA ladder comprises a marker of 135 base pairs (bp) in length and a marker of 146 bp in length;
   e) applying the combined DNA ladder and pooled cDNA from d) to a lane of an agarose gel;
   f) co-migrating by electrophoresis in the lane of the agarose gel the DNA ladder with the pooled cDNA;
   g) cutting the agarose gel between the marker of 135 bp in length and at the marker of 146 bp in length, inclusive,
   h) excising the portion of the agarose gel between the cuts at the marker of 135 bp and at the marker of 146 bp;
   i) extracting cDNA from the excised portion of the agarose gel to obtain a cDNA copy of a microRNA library; and
   j) PCR sequencing the cDNA copy of the microRNA library to identify microRNA sequences in the microRNA library.

2. The method according to claim 1, further comprising determining a concentration of a respective microRNA sequence in the excised portion of the gel.

3. The method according to claim 2, wherein the concentration of the respective microRNA sequence is less than 2.5 ng/µL.

4. The method according to claim 1, further comprising generating the RNA sample and subsequent cDNA therefrom from a reduced amount of input ribonucleic acid of <100 ng in 6 µl.

5. The method according to claim 1, wherein the DNA ladder does not interfere with the sequencing of the 3' adapter.

6. The method according to claim 1, wherein the DNA ladder does not interfere with the sequencing of the 5' adapter.

7. The method of claim 1, wherein the RNA sample comprises microRNA and non-microRNA.

8. The method of claim 7, wherein the non-microRNA comprises piwiRNA.

9. The method of claim 1, wherein the 5' adaptor comprises SEQ ID NO: 1 and the 3' adaptor comprises SEQ ID NO: 2.

10. The method of claim 9, further comprising adding a nucleotide sequence as set forth in SEQ ID NO: 3 and/or SEQ ID NO: 4 to complement the 5' and 3' adaptors respectively.

11. The method of claim 1, wherein the 5' adapter, the 3' adapter, and the microRNA yield a cDNA of 136 to 145 bp in length.

* * * * *

SEQUENCE LISTING

```
<160> NUMBER OF SEQ ID NOS: 6

<210> SEQ ID NO 1
<211> LENGTH: 55
<212> TYPE: DNA
<213> ORGANISM: Artificial Sequence
<220> FEATURE:
<223> OTHER INFORMATION: Synthetic Construct

<400> SEQUENCE: 1
aatgatacgg cgaccaccga gatctacacg ttcagagttc tacagtccga cgatc         55

<210> SEQ ID NO 2
<211> LENGTH: 64
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (25)..(30)
<223> OTHER INFORMATION: n is a, c, g, t or u

<400> SEQUENCE: 2
caagcagaag acggcatacg agatnnnnnn gtgactggag ttcagacgtg tgctcttccg    60
atct                                                                64

<210> SEQ ID NO 3
<211> LENGTH: 33
<212> TYPE: DNA
<213> ORGANISM: Artificial Sequence
<220> FEATURE:
<223> OTHER INFORMATION: Synthetic Construct

<400> SEQUENCE: 3
cgacaggttc agagtttcta cagtccgacg atc                                 33

<210> SEQ ID NO 4
<211> LENGTH: 33
<212> TYPE: DNA
<213> ORGANISM: Artificial Sequence
<220> FEATURE:
<223> OTHER INFORMATION: Synthetic Construct

<400> SEQUENCE: 4
gatcggaaga gcacacgtct gaactccagt cac                                 33

<210> SEQ ID NO 5
<211> LENGTH: 59
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(59)
<223> OTHER INFORMATION: n is a, c, g, t or u
```

<400> SEQUENCE: 5
aatgatacgg cgaccaccga gatctacacg ttcagagttc tacagtccga cgatcnnnn          59

<210> SEQ ID NO 6
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: n is a, c, g, t or u
<220> FEATURE:
<221> NAME/KEY: misc_feature
<222> LOCATION: (37)..(42)
<223> OTHER INFORMATION: n is a, c, g, t or u

<400> SEQUENCE: 6
nnngatcgga agagcacacg tctgaactcc agtcacnnnn nnatctcgta tgccgtcttc          60
tgcttg                                                                     66